United States Patent
Ni et al.

(10) Patent No.: US 10,370,318 B2
(45) Date of Patent: Aug. 6, 2019

(54) METHOD FOR PREPARING ACETIC ACID BY CARBONYLATION OF METHANOL

(71) Applicant: Dalian Institute of Chemical Physics, Chinese Academy of Sciences, Shahekou Dalian (CN)

(72) Inventors: Youming Ni, Dalian (CN); Wenliang Zhu, Dalian (CN); Lei Shi, Dalian (CN); Hongchao Liu, Dalian (CN); Yong Liu, Dalian (CN); Zhongmin Liu, Dalian (CN)

(73) Assignee: Dalian Institute of Chemical Physics, Chinese Academy of Sciences, Shahekou Dalian (CN)

(*) Notice: Subject to any disclaimer, the term of this patent is extended or adjusted under 35 U.S.C. 154(b) by 0 days.

(21) Appl. No.: 15/758,572

(22) PCT Filed: Dec. 8, 2015

(86) PCT No.: PCT/CN2015/096649
§ 371 (c)(1),
(2) Date: Mar. 8, 2018

(87) PCT Pub. No.: WO2017/041373
PCT Pub. Date: Mar. 16, 2017

(65) Prior Publication Data
US 2018/0244599 A1 Aug. 30, 2018

(30) Foreign Application Priority Data
Sep. 11, 2015 (CN) .......................... 2015 1 0578383

(51) Int. Cl.
C07C 53/08 (2006.01)
C07C 51/12 (2006.01)
B01J 29/18 (2006.01)
B01J 29/24 (2006.01)
B01J 29/65 (2006.01)
B01J 29/67 (2006.01)
B01J 31/02 (2006.01)
B01J 31/26 (2006.01)
B01J 37/00 (2006.01)
B01J 37/02 (2006.01)
B01J 37/08 (2006.01)
B01J 37/30 (2006.01)
B01J 29/00 (2006.01)

(52) U.S. Cl.
CPC ............... C07C 51/12 (2013.01); B01J 29/18 (2013.01); B01J 29/24 (2013.01); B01J 29/65 (2013.01); B01J 29/67 (2013.01); B01J 31/0254 (2013.01); B01J 31/26 (2013.01); B01J 37/0072 (2013.01); B01J 37/0203 (2013.01); B01J 37/0207 (2013.01); B01J 37/08 (2013.01); B01J 37/30 (2013.01); C07C 53/08 (2013.01); B01J 29/00 (2013.01); B01J 2229/183 (2013.01)

(58) Field of Classification Search
None
See application file for complete search history.

(56) References Cited

U.S. PATENT DOCUMENTS 5,420,345 A * 5/1995 Smith ..................... C07C 51/12
562/517

FOREIGN PATENT DOCUMENTS

| CN | 1091119 A | 8/1994 |
|---|---|---|
| CN | 101613274 A | 12/2009 |
| CN | 101903325 A | 12/2010 |
| CN | 103896766 | * 12/2012 |
| CN | 103896766 A | 7/2014 |

* cited by examiner

Primary Examiner — Ana Z Muresan
(74) Attorney, Agent, or Firm — Edwin A. Sisson, Attorney at Law, LLC; Jeffrey J. Banyas

(57) ABSTRACT

The present invention provides a method for preparing acetic acid by carbonylation of methanol, which comprises: passing a raw material containing methanol, carbon monoxide and water through a reaction region loaded with a catalyst containing an acidic molecular sieve with an adsorbed organic amine, and carrying out a reaction under the following conditions to prepare acetic acid. The method in the present invention offers high acetic acid selectivity and good catalyst stability. The catalyst in the present invention does not contain noble metals such as rhodium or iridium, and does not need additional agent containing iodine, and thus does not generate a strong corrosive hydroiodic acid and the like.

12 Claims, No Drawings

METHOD FOR PREPARING ACETIC ACID BY CARBONYLATION OF METHANOL

PRIORITIES AND CROSS REFERENCES

This Application claims priority from International Application No. PCT/CN2015/096649 filed on 8 Dec. 2015 and Chinese Application No. 201510578383.5 filed on 11 Sep. 2015, the teachings of each of which are incorporated herein by reference in their entirety.

TECHNICAL FIELD

The present invention refers to a method for preparing acetic acid by carbonylation of methanol.

BACKGROUND

Acetic acid is an important chemical raw material, which is mainly used to produce vinyl acetate, acetic anhydride, acetate and the like. Its global annual output is nearly 10 million tons. Currently, acetic acid is mainly industrial produced by methanol carbonylation routes, typically represented by Monsanto or Cativa™ processes, whose catalyst system is rhodium or iridium coordination compounds (*Adv. Catal.* 53, 2010, 1.). The defects of the two processes which need be further optimized to improve the economic efficiency are listed as follows: firstly, strongly corrosive HI exists in the catalyst recycle process, and thus the reactor must be made from the expensive anti corrosive materials; secondly, the existing industrial process uses homogeneous catalysts, and therefore there is a great energy cost for separation of the products and the catalyst; thirdly, the noble metal catalysts, such as rhodium catalyst or iridium catalyst, are very expensive; fourthly, the product acetic acid may contain trace amount of iodides which will severely affect the quality of acetic acid, to the disadvantage of the production of the acetic acid downstream products.

Fujimoto et al (*Chem. Lett.*, 1984, 2047.) has discovered that methanol can generate acetic acid by a gas phase carbonylation on acidic molecular sieve catalyst. However, the catalyst stability and the selectivity for acetic acid are very low. The main reason is that at low temperature, the water generated from etherification of methanol will cause the passivation of the active centers in the molecular sieve; while at high temperature, methanol will be easily converted into carbon deposit and hydrocarbon. To prevent the impact of water, Iglesia et al have carried out a carbonylation reaction using dimethyl ether on molecular sieve catalyst to prepare methyl acetate (*Angew. Chem. Int. Ed.* 45, 2006, 1617.). In CN101613274A, a method of preparing methyl acetate by carbonylation of dimethyl ether has been disclosed, wherein a mordenite molecular sieve modified by pyridines organic amine is used as the catalyst. However, to obtain acetic acid, this method needs to be combined with processes of preparing dimethyl ether from methanol and hydrolysis of methyl acetate, affecting the economic efficiency.

In WO 2007/128955A1, a method of preparing carboxylic acid and/or its ester by carbonylation of alcohol and/or its derivatives with carbon monoxide has been disclosed, using silver loaded mordenite catalyst or H-typed mordenite catalyst. However, the catalyst stability is not ideal and the selectivity of acetic acid is not high.

SUMMARY OF THE INVENTION

The purpose of the present invention is to provide a method for preparing acetic acid by carbonylation of methanol.

For this purpose, the present invention provides a method for preparing acetic acid by carbonylation of methanol, which comprises: passing a raw material containing methanol, carbon monoxide and water through a reaction region loaded with a catalyst containing an acidic molecular sieve with an adsorbed organic amine, and carrying out a reaction under the following conditions to prepare acetic acid;

wherein the acidic molecular sieve is one or two molecular sieves selected from the group consisting of molecular sieves with MOR framework and molecular sieves with FER framework;

the organic amine is one or more organic amines selected from the group consisting of pyridine, phenylamine, cyclohexylamine, piperidine, substituted pyridines with one or more substituents, substituted phenylamines with one or more substituents, substituted cyclohexylamines with one or more substituents and substituted piperidines with one or more substituents; and the substituents are independently selected from halogen or $C_{1-3}$ alkyl group;

the reaction region is constituted by one or more reactors which are connected in series and/or in parallel;

the reaction conditions are listed as follows: the reaction temperature is in a range from 150° C. to 350° C.; and the reaction pressure is in a range from 0.5 MPa to 10 MPa; and the weight hourly space velocity of methanol is in a range from 0.01 $h^{-1}$ to 10 $h^{-1}$; and the molar ratio of monoxide to methanol is in a range from 1:1 to 100:1; and the molar ratio of water to methanol is in a range from 0.05:1 to 5:1.

The acidic molecular sieve is one or two molecular sieves selected from the group consisting of acidic mordenite molecular sieve and acidic ZSM-35 molecular sieve. Preferably, the acidic molecular sieve is acidic mordenite molecular sieve.

In a preferred embodiment, the atom ratio of Si to Al in the acidic molecular sieve Si/Al is in a range from 3 to 100. Preferably, the atom ratio of Si to Al in the acidic molecular sieve Si/Al is in a range from 5 to 30.

In a preferred embodiment, the acidic molecular sieve contains metal; and the mass fraction of the metal is in a range from 0.1% to 10%. Preferably, the mass fraction of the metal is in a range from 0.1% to 2%.

In a preferred embodiment, the metal is one or more metals selected from the group consisting of copper, iron, gallium, silver, nickel and cobalt.

In a preferred embodiment, the metal is introduced into the acidic molecular sieve by one or more methods selected from the group consisting of in situ synthesis, impregnation and ion exchange.

In a preferred embodiment, the acidic molecular sieve contains a forming agent; and the mass fraction of the forming agent is in a range from 1% to 60%. Preferably the mass fraction of the forming agent is in a range from 10% to 30%.

In a preferred embodiment, the forming agent is one or more materials selected from the group consisting of aluminum oxide, silicon oxide and kaolin.

In a preferred embodiment, the reaction conditions are listed as follows: the reaction temperature is in a range from 240° C. to 300° C.; and the reaction pressure is in a range from 3 MPa to 7 MPa; and the weight hourly space velocity of methanol is in a range from 0.3 $h^{-1}$ to 3.0 $h^{-1}$; and the molar ratio of monoxide to methanol is in a range from 5:1 to 20:1 and the molar ratio of water to methanol is in a range from 0.2:1 to 1:1.

In a preferred embodiment, the reactor is continuous reactor selected from a fixed bed reactor, a moving bed reactor or a fluidized bed reactor.

The advantages of the present invention include, but are not limited to:

a. Compared with the existing technique of preparing acetic acid from methanol carbonylation, the method in the present invention has a great improvement on the selectivity for acetic acid product, which reaches over 95%; and the catalyst stability has been greatly enhanced; and the catalyst activity remains basically unchanged after the reaction running for 1000 hours. It has a great potential for industrial application.

b. Compared with the homogenous phase catalyzing process for preparing acetic acid in the conventional industry, the raw material employed by the method in the present invention does not contain iodide addition agent, without generation of strong corrosive hydroiodic acid (HI). Moreover, there is no iodides contained in the acetic acid product, which can reduce the cost of equipment investment and deep purification of the product. The reaction in the method of the present invention is a muti-phase catalyzing process, which can greatly lower down the energy cost of the separation between the catalyst and the product. The molecular sieve catalyst used in the present invention is very cheap compared with noble metal catalysts, such as rhodium or iridium catalyst.

DETAILED DESCRIPTION OF THE EMBODIMENT

The present invention provides a method for preparing acetic acid by carbonylation of methanol, which comprises: passing a raw material containing methanol, carbon monoxide and water through a reaction region loaded with a catalyst containing an acidic molecular sieve with an adsorbed organic amine, and carrying out a reaction under the following conditions to prepare acetic acid.

In the present invention, the acidic molecular sieve is one or two molecular sieves selected from the group consisting of molecular sieves with MOR framework and molecular sieves with FER framework.

In the present invention, the reaction region is constituted by one or more reactors which are connected in series and/or in parallel.

In the present invention, the organic amine is one or more organic amines selected from the group consisting of pyridine, phenylamine, cyclohexylamine, piperidine, substituted pyridines with one or more substituents, substituted phenylamines with one or more substituents, substituted cyclohexylamines with one or more substituents and substituted piperidines with one or more substituents; and the substituents are independently selected from halogen or $C_{1-3}$ alkyl group.

Preferably, the reaction conditions are listed as follows: the reaction temperature is in a range from 150° C. to 350° C.; and the reaction pressure is in a range from 0.5 MPa to 10 MPa; and the space velocity of methanol is in a range from 0.01 $h^{-1}$ to 10 $h^{-1}$; and the molar ratio of monoxide to methanol is in a range from 1:1 to 100:1; and the molar ratio of water to methanol is in a range from 0.05:1 to 5:1.

The halogen is F, Cl, Br or I.

The $C_{1-3}$ alkyl group is methyl, ethyl, n-propyl or isopropyl.

Although not wished to be bound by any theory, it is discovered by the inventors of the present invention that, in the above mentioned reaction region, the following reactions happened mainly:

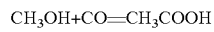  (1)

  (2)

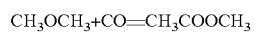  (3)

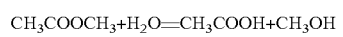  (4)

Reaction (1) is realized through reactions (2) to (4). The equilibrium constant of reaction (4) is relatively small, and the selectivity for acetic acid can be improved by adding water to the raw material of the reaction.

In the present invention, the structural formula of pyridine is

, and the structural formula of phenylamine is

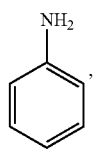, and the structural formula of cyclohexylamine is

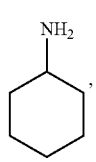, and the structural formula of piperidine is

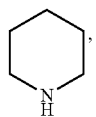, which may also be substituted by one or more groups independently selected from the group consisting of halogen (F, Cl, Br or I) and $C_{1-3}$ alkyl group (e.g. $CH_3$, $C_2H_5$, $C_3H_7$). For example, the substituted pyridine may be:

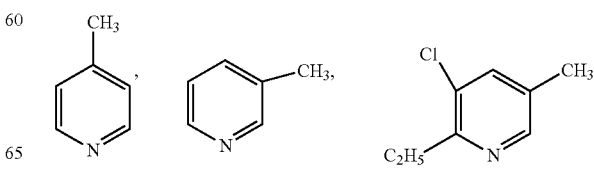

and the like; the substituted phenylamine may be:

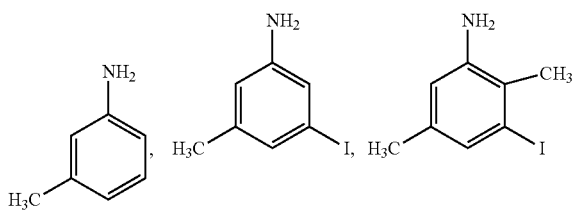

and the like; the substituted cyclohexylamine may be:

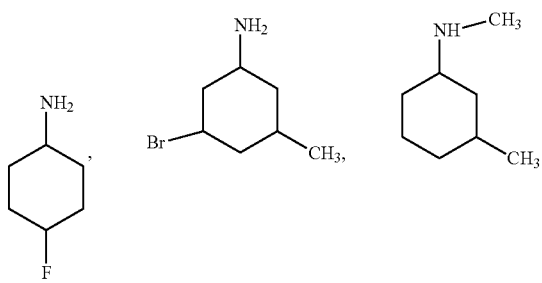

and the like; the substituted piperidine may be:

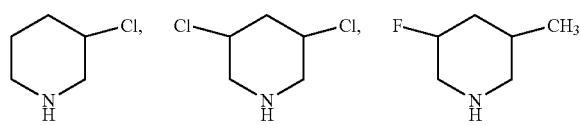

and the like.

In the present invention, the acidic molecular sieve with an absorbed organic amine used as the catalyst, can be prepared by the method comprising the steps listed as follows: loading the acidic molecular sieves catalyst into a reaction tube, and then at an adsorption temperature ranging from 200° C. to 300° C. passing through a mixed gas with a molar content of organic amine ranging from 0.001% to 3%, which contains an organic amine and one or two gases selected from the group consisting of carbon monoxide, hydrogen, nitrogen, air or argon; after reaching to the saturation adsorption, sweeping the catalyst using a mixed gas containing one or two gases selected from the group consisting of carbon monoxide, hydrogen, nitrogen, air or argon at the current temperature for 1 to 6 hours, to obtain the catalyst containing the acidic molecular sieve with an absorbed organic amine. In the catalyst containing the acidic molecular sieve with an absorbed organic amine, and the organic amine is mainly chemically adsorbed.

Preferably, in the present invention, the acidic molecular sieve is one or more molecular sieves selected from the group consisting of acidic mordenite molecular sieve, ZSM-35 molecular sieve, co-crystal molecular sieve containing MOR structural unit, mixed crystal molecular sieve containing MOR structural unit, co-crystal molecular sieve containing FER structural unit and mixed crystal molecular sieve containing FER structural unit. Wherein, the co-crystal molecular sieve containing MOR structural unit means there is not only the MOR structural unit existing, but also other molecular sieve structural unit existing in single crystal of the molecular sieve; and the mixed crystal molecular sieve containing MOR structural unit means there is not only the MOR structural crystal existing, but also other molecular sieve crystal existing in the molecular sieve; the co-crystal molecular sieve containing FER structural unit means there is not only the FER structural unit existing, but also other molecular sieve structural unit existing in single crystal of the molecular sieve; and the mixed crystal molecular sieve containing FER structural unit means there is not only the FER structural crystal existing, but also other molecular sieve crystal existing in the molecular sieve.

More preferably, in the present invention, the acidic molecular sieve is pure phase of mordenite molecular sieve or pure phase of ZSM-35 molecular sieve; further preferably, the acidic molecular sieve is pure phase of mordenite molecular sieve.

Preferably, in the present invention, the atom ratio of Si to Al in the acidic molecular sieve Si/Al is in a range from 3 to 100; more preferably, the atom ratio of Si to Al in the acidic molecular sieve Si/Al is in a range from 5 to 30.

Preferably, in the present invention, the acidic molecular sieve contains metal; and the mass fraction of the metal is in a range from 0.1% to 10%; more preferably the mass fraction of the metal is in a range from 0.1% to 2%.

Preferably, in the present invention, the metal is one or more metals selected from the group consisting of copper, iron, gallium, silver, nickel and cobalt.

Preferably, in the present invention, the location of the metal existing in the molecular sieve is one or more locations selected from the group consisting of the ion exchange sites in the molecular sieve, channels of the molecular sieve, surface of the molecular sieve and the framework of the molecular sieve.

Preferably, in the present invention, the metal is introduced into the acidic molecular sieve by one or more methods selected from the group consisting of in situ synthesis, impregnation and ion exchange.

In the present invention, the metal exists as ions at the ion exchange sites, or exists as metallic oxides in the channel or on the surface of the molecular sieve, or enters into the T atom sites of the molecular framework by isomorphous substitution.

In the present invention, the acidic molecular sieve refers to H type molecular sieve or H type molecular sieve modified by metal.

In the present invention, the acidic molecular sieve may be modified by a desilication post-treatment or a dealumination post-treatment. The dessication post-treatment is an alkaline solution treatment. The alkaline solutions usually used include aqueous solutions of sodium hydroxide, potassium hydroxide, ammonium hydroxide, sodium carbonate- and sodium bicarbonate. The dealuminization post-treatment is an acid solution treatment or a steam treatment. The acid solutions usually used include aqueous solutions of hydrochloric acid, nitric acid, oxalic acid, citric acid and acetic acid. The steam treatment is usually operated at a treating temperature in a range from 400° C. to 700° C.

In the present invention, the acidic molecular sieve may contian one or more structures selected from the group consisting of micrometer structure, nano-structure, microporous structure and meso-microporous structure.

Preferably, in the present invention, the catalyst comprises a forming agent; and the mass fraction of the forming agent is in a range from 1% to 60%. More preferably, in the present invention, the catalyst comprises a forming agent; and the mass fraction of the forming agent is in a range from 10% to 30%.

Preferably, in the present invention, the forming agent is one or more materials selected from the group consisting of aluminum oxide, silicon oxide and kaolin.

In the present invention, the carbon monoxide in the raw material may be carbon monoxide or a raw gas containing carbon monoxide and other gas. Moreover, the raw gas may comprise carbon monoxide, hydrogen, inactive gas and the like; wherein the volume content of the carbon monoxide is in a range from 50% to 100%; and the volume content of the hydrogen is in a range from 0% to 50%; and the volume content of the inactive gas is in a range from 0% to 50%. And the inactive gas comprises one gas or a mixture of several gases, selected from the group consisting of nitrogen, helium, argon, carbon dioxide, methane and ethane. Preferably, the raw gas is syngas. The syngas may be obtained from the conversion of coal, natural gas, petroleum oil or biological substances.

Preferably, in the present invention, the reaction conditions are listed as follows: the reaction temperature is in a range from 240° C. to 300° C.; and the reaction pressure is in a range from 3 MPa to 7 MPa; and the weight hourly space velocity of methanol is in a range from 0.3 $h^{-1}$ to 3.0 $h^{-1}$; and the molar ratio of monoxide to methanol is in a range from 5:1 to 20:1 and the molar ratio of water to methanol is in a range from 0.2:1 to 1:1.

Preferably, in the present invention, the reactor is continuous reactor selected from a fixed bed reactor, a moving bed reactor or a fluidized bed reactor, which can realize continuous reaction. More preferably, the reactor is one or more fixed bed reactors. And the reaction mode is continuous reaction. The fixed bed reactor may be one or more. When several fixed bed reactors are employed, the reactors are connected in series, in parallel or in a combination of in series and in parallel.

EXAMPLES

The present invention is further illustrated in combination with specific Examples as follows. It should be understood that, these Examples are only used for illustrate the present invention but not to limited the scope thereof.

Unless otherwise specified, raw material and catalyst employed in the Examples of the present invention are commercial purchased and directly used.

Analytic method, calculations of conversion rate and selectivity in the Examples are listed as follows:

Gas chromatography Agilent 7890 which has gas automatic sampler, FID detector and FFAP capillary column, are used for automatic analyzing.

In some Examples of the present invention, both the conversion rate and the selectivity are calculated on the basis of the carbon molar number of the methanol:

Percent conversion of methanol=[(carbon molar number of methanol in the feeding material)−(carbon molar number of methanol in the discharging material)]÷(carbon molar number of methanol in the feeding material)×(100%)

Selectivity for acetic acid=1/2×(carbon molar number of acetic acid in the discharging material)÷[(carbon molar number of methanol in the feeding material)−(carbon molar number of methanol in the discharging material)]×(100%)

The present invention is described in details by the following Examples, but the invention is not limited to these Examples.

Preparation of the Catalyst

Example 1

1 kg of Na-type mordenite (Si/Al=7) was exchanged with 0.8 mol/L of ammonium nitrate aqueous solution at 80° C. for three times to obtain an ammonium-type mordenite. And then the ammonium-type mordenite was calcined at 550° C. for 4 h in air to obtain an H-type mordenite. The H-type mordenite was pressed, crushed and sieved to 5-10 mesh to obtain a particle sample. And then, the particle sample was loaded into a stainless steel fixed bed reactor with a diameter of 32 mm, and then was treated with a 500 ml/min mixed gas of pyridine and nitrogen with pyridine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic mordenite molecular sieve with absorbed pyridine which was used as the Catalyst A. The composition of the Catalyst A is shown in Table 1.

Example 2

1 kg of Na-type mordenite (Si/Al=30) was exchanged with 0.8 mol/L of ammonium nitrate aqueous solution at 80° C. for three times to obtain an ammonium-type mordenite. And then the ammonium-type mordenite was calcined at 550° C. for 4 h in air to obtain an H-type mordenite. The H-type mordenite was pressed, crushed and sieved to 5-10 mesh to obtain a particle sample. And then, the particle sample was loaded into a stainless steel fixed bed reactor with a diameter of 32 mm, and then was treated with a 500 ml/min mixed gas of pyridine and nitrogen with pyridine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic mordenite molecular sieve with absorbed pyridine which was used as the Catalyst B. The composition of the Catalyst B is shown in Table 1.

Example 3

1 kg of Na-type ZSM-35 (Si/Al=3) was exchanged with 0.8 mol/L of ammonium nitrate aqueous solution at 80° C. for three times to obtain an ammonium-type ZSM-35. And then the ammonium-type ZSM-35 was calcined at 550° C. for 4 h in air to obtain an H-type ZSM-35. The H-type ZSM-35 was pressed, crushed and sieved to 5-10 mesh to obtain a particle sample. And then, the particle sample was loaded into a stainless steel fixed bed reactor with a diameter of 32 mm, and then was treated with a 500 ml/min mixed gas of phenylamine and nitrogen with phenylamine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic ZSM-35 molecular sieve with absorbed phenylamine which was used as the Catalyst C. The composition of the Catalyst C is shown in Table 1.

Example 4

1 kg of Na-type ZSM-35 (Si/Al=15) was exchanged with 0.8 mol/L of ammonium nitrate aqueous solution at 80° C. for three times to obtain an ammonium-type ZSM-35. And then the ammonium-type ZSM-35 was calcined at 550° C. for 4 h in air to obtain an H-type ZSM-35. The H-type ZSM-35 was pressed, crushed and sieved to 5-10 mesh to obtain a particle sample. And then, the particle sample was loaded into a stainless steel fixed bed reactor with a diameter of 32 mm, and then was treated with a 500 ml/min mixed gas of cyclohexylamine and nitrogen with cyclohexylamine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic ZSM-35 molecular sieve with absorbed cyclohexylamine which was used as the Catalyst D. The composition of the Catalyst D is shown in Table 1.

Example 5

1 kg of mordenite (Si/Al=100) was exchanged with 0.8 mol/L of ammonium nitrate aqueous solution at 80° C. for three times to obtain an ammonium-type co-crystal molecular sieve. And then the ammonium-type co-crystal molecular sieve was calcined at 550° C. for 4 h in air to obtain an H-type co-crystal molecular sieve. The H-type co-crystal molecular sieve was pressed, crushed and sieved to 5-10 mesh to obtain a particle sample. And then, the particle sample was loaded into a stainless steel fixed bed reactor with a diameter of 32 mm, and then was treated with a 500 ml/min mixed gas of piperidine and nitrogen with piperidine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic mordenite molecular sieve with absorbed piperidine which was used as the Catalyst E. The composition of the Catalyst E is shown in Table 1.

Example 6

1 kg of Na-type mordenite (Si/Al=20) was exchanged with 0.8 mol/L of ammonium nitrate aqueous solution at 80° C. for three times to obtain an ammonium-type mixed crystal molecular. And then the ammonium-type mixed crystal molecular sieve was calcined at 550° C. for 4 h in air to obtain a H-type mixed crystal molecular sieve. And then, the H-type mordenite molecular sieve was extruded with 20 wt % aluminum oxide to form a rod like sample of Φ3 mm×3 mm. And then, the rod like sample was loaded into a stainless steel fixed bed reactor with a diameter of 32 mm, and then was treated with a 500 ml/min mixed gas of 4-methylpyridine and nitrogen with 4-methylpyridine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic mordenite molecular sieve with absorbed 4-methylpyridine which was used as the Catalyst F. The composition of the Catalyst F is shown in Table 1.

Example 7

1 kg of Na-type mordenite (Si/Al=7) was exchanged with 0.8 mol/L of ammonium nitrate aqueous solution at 80° C. for three times to obtain an ammonium-type mordenite. The ammonium type mordenite was ion exchanged with 0.1 mol/L copper nitrate aqueous solution at 80° C. to obtain an ammonium type mordenite with a copper content of 1 wt %. And then the ammonium-type mordenite with a copper content of 1 wt % was calcined at 550° C. for 4 h in air to obtain an H-type mordenite. And then, the H-type mordenite was extruded with 20 wt % aluminum oxide to form a rod like sample of Φ3 mm×3 mm. And then, the rod like sample was loaded into a stainless steel fixed bed reactor with a diameter of 32 mm, and then was treated with a 500 ml/min mixed gas of 4-chloropyridine and nitrogen with 4-chloropyridine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to obtain an acidic mordenite molecular sieve containing copper with absorbed 4-chloropyridine which was used as the Catalyst G The composition of the Catalyst G is shown in Table 1.

Example 8

1 kg of Na-type ZSM-35 (Si/Al=15) was exchanged with 0.8 mol/L of ammonium nitrate aqueous solution at 80° C. for three times to obtain an ammonium-type ZSM-35. The ammonium type ZSM-35 was ion exchanged with 0.1 mol/L silver nitrate aqueous solution at 80° C. to obtain an ammonium type ZSM-35 with a silver content of 0.5 wt %. And then the ammonium-type ZSM-35 with a silver content of 0.5 wt % was calcined at 550° C. for 4 h in air to obtain an H-type ZSM-35 with a silver content of 0.5 wt %. And then, the H-type ZSM-35 with a silver content of 0.5 wt % was extruded with 20 wt % aluminum oxide to form a rod like sample of Φ3 mm×3 mm. And then, the rod like sample was loaded into a stainless steel fixed bed reactor with a diameter of 32 mm, and then was treated with a 500 ml/min mixed gas of cyclohexylamine and nitrogen with cyclohexylamine molar concentration of 0.3% for 6 h to the saturation adsorption at 280° C. and atmospheric pressure; and then was swept using 500 ml/min nitrogen for 3 h at 280° C. and atmospheric pressure; and then was cooled to the room temperature to the obtain an acidic ZSM-35 molecular sieve containing silver with absorbed cyclohexylamine which was used as the Catalyst H. The composition of the Catalyst H is shown in Table 1.

Comparative Example 1

1 kg of Na-type mordenite (Si/Al=7) was exchanged with 0.8 mol/L of ammonium nitrate aqueous solution at 80° C. for three times to obtain an ammonium-type mordenite. And then the ammonium-type mordenite was calcined at 550° C. for 4 h in air to obtain an H-type mordenite. The H-type mordenite was pressed, crushed and sieved to 5-10 mesh to obtain a particle sample as Catalyst I. The composition of the Catalyst I is shown in Table 1.

Comparative Example 2

1 kg of Na-type ZSM-35 (Si/Al=15) was exchanged with 0.8 mol/L of ammonium nitrate aqueous solution at 80° C. for three times to obtain an ammonium-type ZSM-35. And then the ammonium-type ZSM-35 was calcined at 550° C. for 4 h in air to obtain a H-type ZSM-35. The H-type ZSM-35 was pressed, crushed and sieved to 5-10 mesh to obtain a particle sample as Catalyst J. The composition of the Catalyst J is shown in Table 1.

TABLE 1

Composition of the catalysts in Examples 1 to 8 and Comparative Examples 1 and 2

| Example/ Comparative Example | Catalyst No. | Molecular sieve types in the catalysts | Silicon and aluminum ratio of the molecular sieves (Si/Al) | Metal content of the molecular sieve in the catalysts | Organic amines adsorbed in catalysts | Forming agent in catalysts and their content |
|---|---|---|---|---|---|---|
| Example 1 | A | mordenite | 7 | no | pyridine | no |
| Example 2 | B | mordenite | 30 | no | pyridine | no |
| Example 3 | C | ZSM-35 | 3 | no | phenylamine | no |
| Example 4 | D | ZSM-35 | 15 | no | cyclohexylamine | no |
| Example 5 | E | mordenite | 100 | no | piridine | no |
| Example 6 | F | mordenite | 20 | no | 4-methyl-pyridine | 20% aluminum oxide |
| Example 7 | G | mordenite | 7 | 1% copper | 4-chloro-pyridine | 20% aluminum oxide |
| Example 8 | H | ZSM-35 | 15 | 0.5% silver | cyclohexyl-amine | 20% aluminum oxide |
| Comparative Example 1 | I | mordenite | 7 | no | no | no |
| Comparative Example 2 | J | ZSM-35 | 15 | no | no | no |

Preparing Acetic Acid by Carbonylation of Methanol

Example 9

100 g of Catalyst A was put into a stainless steel tube reactor with inner diameter of 32 mm, and then reacting under the following conditions: reaction temperature was 260° C., and reaction pressure was 5 MPa, and weight hourly space velocity of methanol was 0.5 h$^{-1}$, and molar ratio of carbon monoxide to methanol was 10:1, and molar ratio of water to methanol was 0.05:1. After the reaction was stable, the product was analyzed by gas chromatography, and the Percent conversion of methanol and the selectivity for acetic acid were calculated. The reaction results are shown in Table 2.

Example 10

100 g of Catalyst B was put into a stainless steel tube reactor with inner diameter of 32 mm, and then reacting under the following conditions: reaction temperature was 240° C., and reaction pressure was 7 MPa, and weight hourly space velocity of methanol was 3 h$^{-1}$, and molar ratio of carbon monoxide to methanol was 70:1, and molar ratio of water to methanol was 1:1. After the reaction was stable, the product was analyzed by gas chromatography, and the Percent conversion of methanol and the selectivity for acetic acid were calculated. The reaction results are shown in Table 2.

Example 11

100 g of Catalyst C was put into a stainless steel tube reactor with inner diameter of 32 mm, and then reacting under the following conditions: reaction temperature was 200° C., and reaction pressure was 10 MPa, and weight hourly space velocity of methanol was 0.3 h$^{-1}$, and molar ratio of carbon monoxide to methanol was 20:1, and molar ratio of water to methanol was 0.2:1. After the reaction was stable, the product was analyzed by gas chromatography, and the Percent conversion of methanol and the selectivity for acetic acid were calculated. The reaction results are shown in Table 2.

Example 12

100 g of Catalyst D was put into a stainless steel tube reactor with inner diameter of 32 mm, and then reacting under the following conditions: reaction temperature was 270° C., and reaction pressure was 3 MPa, and weight hourly space velocity of methanol was 6 h$^{-1}$, and molar ratio of carbon monoxide to methanol was 15:1, and molar ratio of water to methanol was 2:1. After the reaction was stable, the product was analyzed by gas chromatography, and the Percent conversion of methanol and the selectivity for acetic acid were calculated. The reaction results are shown in Table 2.

Example 13

100 g of Catalyst E was put into a stainless steel tube reactor with inner diameter of 32 mm, and then reacting under the following conditions: reaction temperature was 150° C., and reaction pressure was 0.5 MPa, and weight hourly space velocity of methanol was 0.01 h$^{-1}$, and molar ratio of carbon monoxide to methanol was 100:1, and molar ratio of water to methanol was 0.08:1. After the reaction was stable, the product was analyzed by gas chromatography, and the Percent conversion of methanol and the selectivity for acetic acid were calculated. The reaction results are shown in Table 2.

Example 14

100 g of Catalyst F was put into a stainless steel tube reactor with inner diameter of 32 mm, and then reacting under the following conditions: reaction temperature was 350° C., and reaction pressure was 8 MPa, and weight hourly space velocity of methanol was 10 h$^{-1}$, and molar ratio of carbon monoxide to methanol was 1:1, and molar ratio of water to methanol was 5:1. After the reaction was stable, the product was analyzed by gas chromatography, and the Percent conversion of methanol and the selectivity for acetic acid were calculated. The reaction results are shown in Table 2.

Example 15

100 g of Catalyst G was put into a stainless steel tube reactor with inner diameter of 32 mm, and then reacting under the following conditions: reaction temperature was 260° C., and reaction pressure was 5 MPa, and weight hourly space velocity of methanol was 0.5 $h^{-1}$, and molar ratio of carbon monoxide to methanol was 5:1, and molar ratio of water to methanol was 0.3:1. After the reaction was stable, the product was analyzed by gas chromatography, and the Percent conversion of methanol and the selectivity for acetic acid were calculated. The reaction results are shown in Table 2.

Example 16

100 g of Catalyst H was put into a stainless steel tube reactor with inner diameter of 32 mm, and then reacting under the following conditions: reaction temperature was 270° C., and reaction pressure was 3 MPa, and weight hourly space velocity of methanol was 6 $h^{-1}$, and molar ratio of carbon monoxide to methanol was 50:1, and molar ratio of water to methanol was 0.5:1. After the reaction was stable, the product was analyzed by gas chromatography, and the Percent conversion of methanol and the selectivity for acetic acid were calculated. Results of the reaction are shown in Table 2.

Comparative Example 3

Catalyst in Example 9 was replaced by Catalyst I, and operating steps and other conditions were the same as Example 9. The reaction results are shown in Table 2.

Comparative Example 4

Catalyst in Example 12 was replaced by Catalyst J, and operating steps and other conditions were the same as Example 12. The reaction results are shown in Table 2.

TABLE 2

Results of the catalytic reaction in Examples 9 to 16 and Comparative Examples 3 and 4

| Examples/ Comparative Example | Catalyst | Reaction temperature/Reaction pressure/Weight hourly space velocity of methanol/carbon monoxide:methanol/ water:methanol | Reaction time (h) | Percent conversion of methanol (%) | Selectivity for acetic acid (%) |
|---|---|---|---|---|---|
| Example 9 | A | 260□/5 MPa/0.5 $h^{-1}$/10:1/0.05:1 | 10 | 100 | 97.8 |
| | | | 100 | 100 | 97.7 |
| | | | 1000 | 100 | 97.5 |
| Example 10 | B | 240□/7 MPa/3 $h^{-1}$/70:1/1:1 | 10 | 100 | 95.4 |
| | | | 100 | 100 | 95.2 |
| | | | 1000 | 100 | 95.1 |
| Example 11 | C | 200□/10 MPa/0.3 $h^{-1}$/20:1/0.2:1 | 10 | 60.0 | 96.8 |
| | | | 100 | 59.8 | 96.7 |
| | | | 1000 | 59.5 | 96.7 |
| Example 12 | D | 270□/3 MPa/6 $h^{-1}$/15:1/2:1 | 10 | 100 | 98.2 |
| | | | 100 | 100 | 98.1 |
| | | | 1000 | 100 | 98.0 |
| Example 13 | E | 150□/0.5 MPa/0.01 $h^{-1}$/100:1/0.08:1 | 10 | 50.9 | 99.1 |
| | | | 100 | 50.4 | 99.0 |
| | | | 1000 | 50.2 | 98.9 |
| Example 14 | F | 350□/8 MPa/0.5 $h^{-1}$/1:1/5:1 | 10 | 100 | 95.3 |
| | | | 100 | 100 | 95.2 |
| | | | 1000 | 100 | 95.1 |
| Example 15 | G | 260□/5 MPa/0.5 $h^{-1}$/5:1/0.3:1 | 10 | 100 | 99.6 |
| | | | 100 | 100 | 99.4 |
| | | | 1000 | 100 | 99.2 |
| Example 16 | H | 270□/3 MPa/6 $h^{-1}$/50:1/0.5:1 | 10 | 100 | 96.5 |
| | | | 100 | 100 | 96.2 |
| | | | 1000 | 100 | 96.0 |
| Comparative example 3 | I | 260□/5 MPa/0.5 $h^{-1}$/10:1/0.05:1 | 2 | 100 | 96.3 |
| | | | 5 | 50.0 | 52.7 |
| | | | 10 | 5.8 | 6.8 |
| Comparative example 4 | J | 270□/3 MPa/6 $h^{-1}$/15:1/2:1 | 2 | 100 | 88.6 |
| | | | 5 | 41.6 | 33.6 |
| | | | 10 | 2.6 | 5.0 |

The present invention has been described in detail as above, but the invention is not limited to the detailed embodiments described in this text. Those skilled in the art will understand that other changes and deformations can be made without deviating from the scope of the invention. The scope of the invention is limited by the appended claims.

The invention claimed is:
1. A method for preparing acetic acid by carbonylation of methanol, which comprises: passing a raw material containing methanol, carbon monoxide and water through a reaction region loaded with a catalyst containing an acidic molecular sieve with an adsorbed organic amine, and carrying out a reaction under the following conditions to prepare acetic acid;
wherein the acidic molecular sieve is one or two molecular sieves selected from the group consisting of molecular sieves with MOR framework and molecular sieves with FER framework;
the organic amine is one or more organic amines selected from the group consisting of pyridine, phenylamine, cyclohexylamine, piperidine, substituted pyridines with one or more substituents, substituted phenylam- ines with one or more substituents, substituted cyclohexylamines with one or more substituents and substituted piperidines with one or more substituents; and the substituents are independently selected from halogen or $C_{1-3}$ alkyl group;

the reaction region is constituted by one or more reactors which are connected in series and/or in parallel;

the reaction conditions are listed as follows: the reaction temperature is in a range from 150° C. to 350° C.; and the reaction pressure is in a range from 0.5 MPa to 10 MPa; and the weight hourly space velocity of methanol is in a range from 0.01 $h^{-1}$ to 10 $h^{-1}$; and the molar ratio of monoxide to methanol is in a range from 1:1 to 100:1; and the molar ratio of water to methanol is in a range from 0.05:1 to 5:1; and wherein the acidic molecular sieve is an acidic mordenite molecular sieve.

2. The method according to claim 1, wherein the atom ratio of Si to Al in the acidic molecular sieve Si/Al is in a range from 3 to 100.

3. The method according to claim 1, wherein the acidic molecular sieve contains metal; and the mass fraction of the metal is in a range from 0.1% to 10%.

4. The method according to claim 3, wherein the metal is one or more metals selected from the group consisting of copper, iron, gallium, silver, nickel and cobalt.

5. The method according to claim 3, wherein the metal is introduced into the acidic molecular sieve by one or more methods selected from the group consisting of in situ synthesis, impregnation and ion exchange.

6. The method according to claim 1, wherein the acidic molecular sieve contains a forming agent; and the mass fraction of the forming agent is in a range from 1% to 60%.

7. The method according to claim 6, wherein the forming agent is one or more materials selected from the group consisting of aluminum oxide, silicon oxide and kaolin.

8. The method according to claim 1, wherein the reaction conditions are listed as follows: the reaction temperature is in a range from 240° C. to 300° C.; and the reaction pressure is in a range from 3 MPa to 7 MPa; and the weight hourly space velocity of methanol is in a range from 0.3 $h^{-1}$ to 3.0 $h^1$; and the molar ratio of monoxide to methanol is in a range from 5:1 to 20:1 and the molar ratio of water to methanol is in a range from 0.2:1 to 1:1.

9. The method according to claim 1, wherein the reactor is continuous reactor selected from a fixed bed reactor, a moving bed reactor or a fluidized bed reactor.

10. The method according to claim 1, wherein the atom ratio of Si to Al in the acidic molecular sieve Si/Al is in a range from 5 to 30.

11. The method according to claim 3, wherein the mass fraction of the metal is in a range from 0.1% to 2%.

12. The method according to claim 6, wherein the mass fraction of the forming agent is in a range from 10% to 30%.

* * * * *